(12) United States Patent
Hein et al.

(10) Patent No.: US 8,175,218 B2
(45) Date of Patent: May 8, 2012

(54) INTERPOLATION INTERLACING BASED DATA UPSAMPLING ALGORITHM FOR CONE-BEAM X-RAY CT FLYING FOCAL SPOT PROJECTION DATA

(75) Inventors: Ilmar Hein, Chicago, IL (US);
Aleksandr Zamyatin, Buffalo Grove, IL (US)

(73) Assignees: Kabushiki Kaisha Toshiba, Tokyo (JP);
Toshiba Medical Systems Corporation, Otawara-shi (JP)

( * ) Notice: Subject to any disclaimer, the term of this patent is extended or adjusted under 35 U.S.C. 154(b) by 688 days.

(21) Appl. No.: 12/244,624

(22) Filed: Oct. 2, 2008

(65) Prior Publication Data
US 2009/0110257 A1    Apr. 30, 2009

Related U.S. Application Data

(60) Provisional application No. 60/983,536, filed on Oct. 29, 2007.

(51) Int. Cl.
*A61B 6/03* (2006.01)
(52) U.S. Cl. ............................... 378/19; 378/4; 382/131
(58) Field of Classification Search ................ 378/4, 19; 382/128–132
See application file for complete search history.

(56) References Cited

U.S. PATENT DOCUMENTS

| | | | |
|---|---|---|---|
| 7,769,129 B2 * | 8/2010 | Hein et al. ........................ 378/19 |
| 2004/0081279 A1 * | 4/2004 | Brunnett ....................... 378/98.8 |
| 2005/0152490 A1 * | 7/2005 | Shechter ........................... 378/4 |
| 2009/0238328 A1 * | 9/2009 | Forthmann et al. ............. 378/14 |

OTHER PUBLICATIONS

Hein et al., A weighted zero-interlacing based native-geometry flying focal spot data upsampling algorithm for cone-beam x-ray CT, Jul. 11, 2007, 9th International Meeting on Fully Three-dimensional Image Reconstruction in Radiology and Nuclear Medicine, pp. 257-260 of proceedings.*
Shechter et al., High-resolution images of Cone Beam Collimated CT Scans, 2004, IEEE pp. 2973-2977.*

* cited by examiner

*Primary Examiner* — Edward Glick
*Assistant Examiner* — John Corbett
(74) *Attorney, Agent, or Firm* — Oblon, Spivak, McClelland, Maier & Neustadt, L.L.P.

(57) ABSTRACT

A method of computed-tomography and a computed-tomography apparatus where a flying focal spot x-ray interpolation interlacing is used. Weighted or non-weighted interlacing of zero values is performed, or interpolation interlacing is performed. The interpolation interlacing may be implemented as part of backprojection and or may be a separate process prior to backprojection. In both cases interlacing is performed on post-logged convolved data. The interpolation interlacing may also be incorporated into different parts of the processing chain, such as before convolution.

18 Claims, 7 Drawing Sheets

INTERPOLATION INTERLACING BASED DATA UPSAMPLING ALGORITHM FOR CONE-BEAM X-RAY CT FLYING FOCAL SPOT PROJECTION DATA

BACKGROUND OF THE INVENTION

1. Field of the Invention

The present invention relates to computed tomographic (CT) imaging, and in particular to CT imaging with interlacing based data upsampling.

2. Discussion of the Background

Images produced from helical multislice CT systems exhibit a distinct type of artifact when operated at medium and high helical pitch values. The artifacts appear as alternating light and dark regions around structures whose features change axially. The shape of the artifact is similar to the vanes on a windmill, hence the name "windmill" artifact (this artifact has also been referred to as simply the "helical" artifact in the literature.)

The cause of the windmill artifact is insufficient sampling by the detectors in the axial direction. The windmill artifact can be decreased or eliminated if axial sampling (resolution) can be increased by decreasing the size of the detector in the axial direction. However, this is not a practical alternative since detectors are already at the smallest limit supported by the current level of technology.

One method of increasing the axial sampling without physically reducing the size of the detectors is to implement an x-ray tube with a flying focal spot is described in U.S. Pat. No. 6,256,369, and is shown in FIG. 1. $R_{EB}$ represents the position of the electron beam on the anode in the radial direction, which, due to the angled shape of the anode, has a corresponding focal spot position $z_{fs}$ in the axial direction. The nominal source-object and source detector distances are SOD and SDD, with nominal detector size at isocenter w. Deflection of the electron beam position $R_{EB}$ to $\pm\Delta$SOD results in two focal spots at $z_{fs}=\pm\delta$ in the axial direction (with actual source-object and source-detector distances SOD$\pm\Delta$SOD and SDD$\pm\Delta$SOD). When $\delta$ is calculated to produce an offset of one quarter of the detector widths at isocenter (see Stierstorfer Flohr, "A Reconstruction Procedure for CT Systems with z-Sharp Technology," Proc. 8th Annual Meeting on Fully Three Dimensional Image Reconstruction in Radiology and Nuclear Medicine, July 2005, pp. 28-30).

$$\delta = \frac{1}{4}\frac{w \cdot SDD}{(SDD - SOD)} \quad (1)$$

the detector segments of adjacent views will overlap by half their width:

$$w_{FFS} = \frac{w}{2} \quad (2)$$

Simply backprojecting the flying focal spot data as-is will not result in a doubling of axial sampling density with little or no windmill artifact reduction, since the width of the detectors is still w.

Siemens incorporates a flying focal spot in their Sensation 64 CT scanner for the same application. In their implementation, while exact, the projection data is rebinned and resampled in both the longitudinal and azimuthal direction into a parallel geometry, and then reconstructed (see Kachelreiβ, Knaup, Penβell, and Kalender; "Flying Focal Spot in Cone-Beam CT," IEEE Transactions on Nuclear Science, Vol. 53, No. 3, June, 2006, pp. 1238-1247, and Stierstorfer et al., supra. Philips also has described a rebinning and resampling to parallel reconstruction algorithm for flying focal spot in Shechter, Koehler, Altman, and Proksa, "High-Resolution Images of Cone-Beam Collimated Scans," IEEE Transactions on Nuclear Science, Vol. 52, No. 1, February, 2005, pp. 247-255. Rebinning and resampling is a time-consuming task that does not lend itself easily to cone-beam geometry. It also requires approximately twice the number of views to obtain the same signal-to-noise ratio as the non-flying focal spot case.

A common zero-interlacing applications is increasing the data rate of a digitized signal (see Elliot, Douglas, ed., *Handbook of Digital Signal Processing: Engineering Applications*, Academic Press, Inc., 1987, pp. 234-237; also referred to as "zero packing"). If a digitized signal is sampled with some period T, the data can be upsampled by a factor of N to T/N by packing the upsampled data values with zeroes, taking the FFT, low pass filtering, and then taking the inverse FFT. This resulting upsampled values are interpolated values, however, and do not represent a true increase in the sampling density. If implemented without flying focal spot, it would have little or no effect on the windmill artifact.

A "zero-interleaving" technique applied to CT was described in Shechter, Koehler, Altman, and Proksa, "High-Resolution Images of Cone-Beam Collimated Scans," IEEE Transactions on Nuclear Science, Vol. 52, No. 1, February, 2005, pp. 247-25. In that technique, zero-interleaving of data in the channel direction was used to implement a faster version of the ray offset technique improving transaxial resolution. This is not a flying focal spot algorithm and has no increase in sampling in the axial direction. Additionally, like the above Siemens approach, it requires rebinning and resampling into a parallel geometry.

SUMMARY OF THE INVENTION

The present invention is directed to a computed-tomography method of and apparatus for interpolation interlacing. The computed-tomography apparatus, in one embodiment, may include a flying focal point x-ray source, an x-ray detector disposed to receive x-rays from the x-ray source, a unit to collect projection data generated by the detector, a processing unit configured to perform interpolation interlacing using the projection data and to reconstruct an image, and a display.

The method of computed-tomography, in one embodiment, may include exposing a subject to x-rays from a flying focal point x-ray source, collecting projection data from the x-rays, performing interpolation interlacing using the projection data and to reconstruct an image and displaying the image. The interpolation interlacing may comprise zero interlacing upsampling or weighted zero interlacing upsampling.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION

Figure 2:
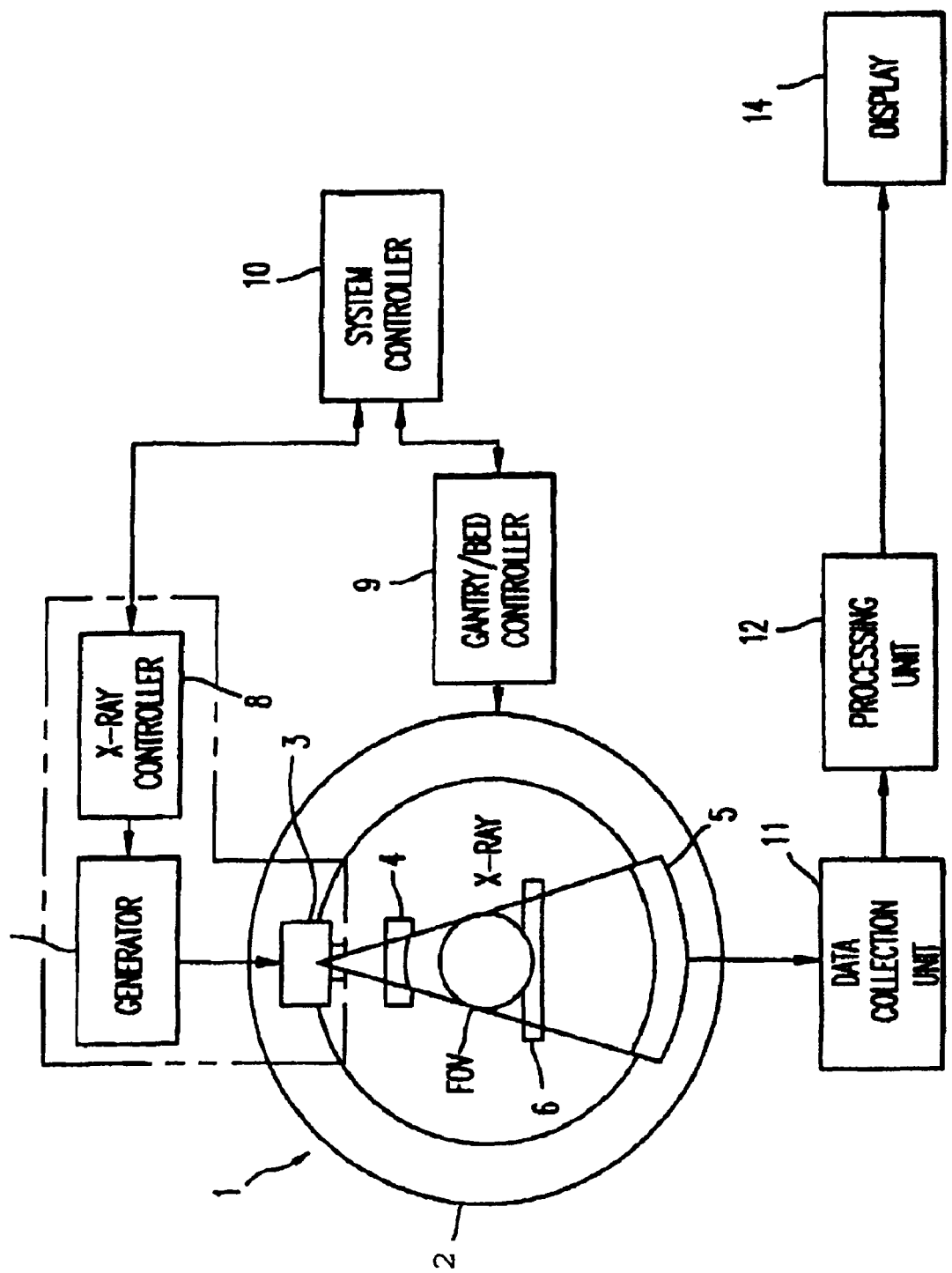
FIG. 2 is a diagram of a system according to the invention.

FIG. 2 shows an x-ray computed tomographic imaging device that can be used to obtain data processed by methods of the present invention. The projection data measurement system constituted by gantry 1 accommodates an x-ray source 3 that generates a cone-beam of x-ray flux approximately cone-shaped, and a two-dimensional array type x-ray detector 5 consisting of a plurality of detector elements arranged in two-dimensional fashion, i.e., a plurality of elements arranged in one dimension stacked in a plurality of rows. X-ray source 3 and two-dimensional array type x-ray detector 5 are installed on a rotating ring 2 in facing opposite sides of a subject, who is laid on a sliding sheet of a bed 6. Two-dimensional array type x-ray detector 5 is mounted on rotating ring 2. Each detector element will correspond with one channel. X-rays from x-ray source 3 are directed on to subject through an x-ray filter 4. X-rays that have passed through the subject are detected as an electrical signal by two-dimensional array type x-ray detector 5.

X-ray controller 8 supplies a trigger signal to high voltage generator 7. High voltage generator 7 applies high voltage to x-ray source 3 with the timing with which the trigger signal is received. This causes x-rays to be emitted from x-ray source 3. Gantry/bed controller 9 synchronously controls the revolution of rotating ring 2 of gantry 1 and the sliding of the sliding sheet of bed 6. System controller 10 constitutes the control center of the entire system and controls x-ray controller 8 and gantry/bed controller 9 such that, as seen from the subject, x-ray source 3 executes so-called helical scanning, in which it moves along a helical path. Specifically, rotating ring 2 is continuously rotated with fixed angular speed while the sliding plate is displaced with fixed speed, and x-rays are emitted continuously or intermittently at fixed angular intervals from x-ray source 3.

The output signal of two-dimensional array type x-ray detector 5 is amplified by a data collection unit 11 for each channel and converted to a digital signal, to produce projection data. The projection data output from data collection unit 11 is fed to processing unit 12. Processing unit 12 performs various processing using the projection data. Unit 12 performs interpolation interlacing (as described in more detail below), backprojection and reconstruction. Unit 12 determines backprojection data reflecting the x-ray absorption in each voxel. In the helical scanning system using a cone-beam of x-rays, the imaging region (effective field of view) is of cylindrical shape of radius o) centered on the axis of revolution. Unit 12 defines a plurality of voxels (three-dimensional pixels) in this imaging region, and finds the backprojection data for each voxel. The three-dimensional image data or tomographic image data compiled by using this backprojection data is sent to display device 14, where it is displayed visually as a three-dimensional image or tomographic image.

Figure 3:
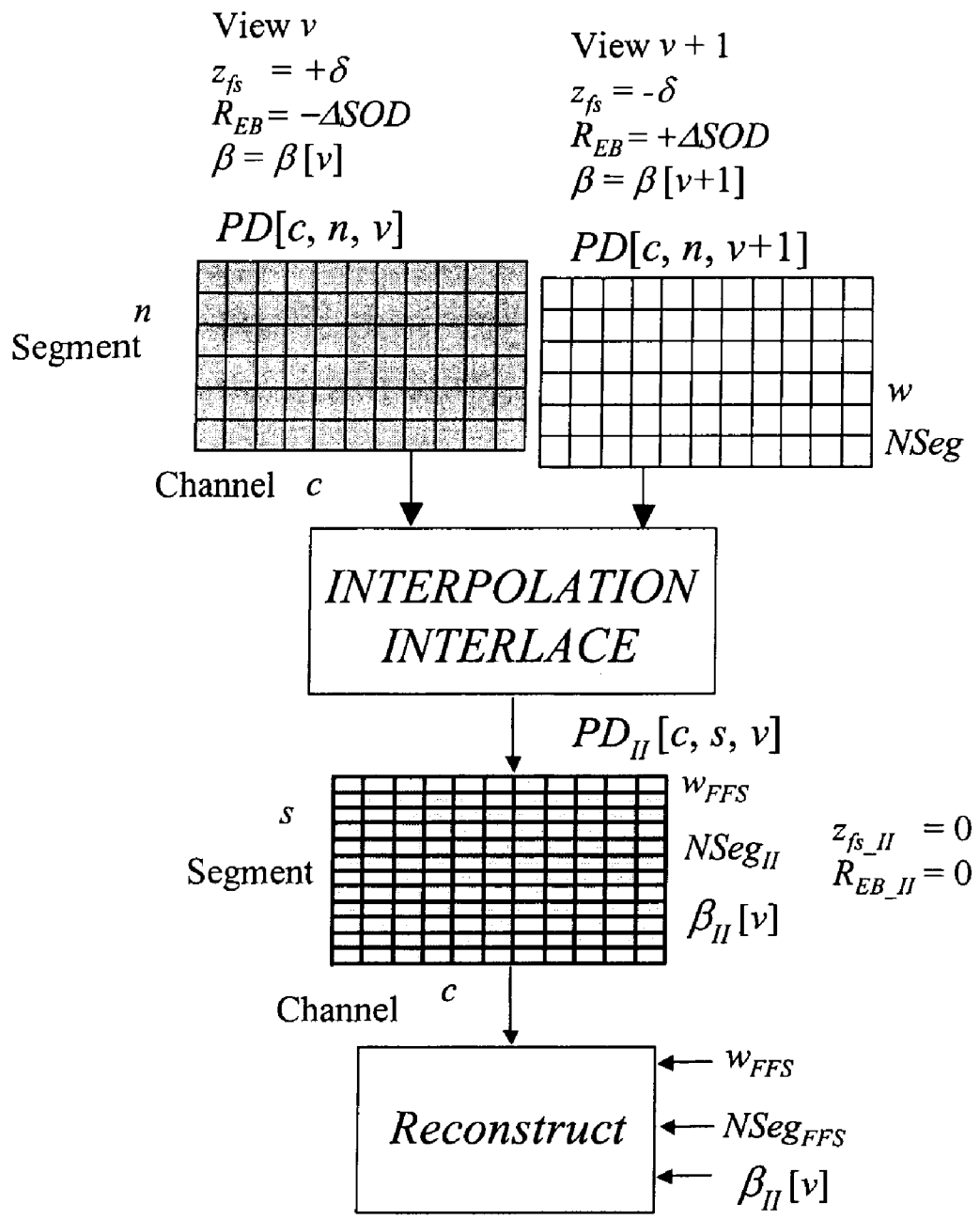
FIG. 3 is a diagram of interlacing processing according to a first embodiment of the invention.

FIG. 3 is a block diagram of the interpolation-interlacing algorithm according to a first embodiment of the invention. The input data PD[ ] is post-logged, convolved projection data, and each interpolated view v is created from input views v and v+1. The output parameters are given by:

$$w_{FFS} = \frac{w}{2} \quad (3)$$

$$NSeg_{II} = 2 \cdot NSeg + 1 \quad (4)$$

$$\beta_{II}[v] = \frac{\beta[v] + \beta[v+1]}{2} \quad (5)$$

$$zfs_{II} = 0 \quad (6)$$

$$R_{EB\_II} = 0 \quad (7)$$

where NSeg and $NSeg_{FFS}$ are the input and output number of segments and $\beta[v]$ is the view angle at view v.

The interpolation interlacing of data is given in Eq. 8:

$$PD_{II}[c, s, v] = \quad (8)$$

$$\begin{cases} W_{II1} \cdot PD[c, 0, v] + \\ W_{II2} \cdot PD[c, 0, v+1] & s = 0 \\ W_{II1} \cdot PD[c, A, v] + \\ W_{II2} \cdot PD[c, n, v+1] & 1 \le s < NSeg_{FFS} - 1; z_{fs}(v) = +\delta \\ W_{II1} \cdot PD[c, n, v] + \\ W_{II2} \cdot PD[c, n - \text{even}(s), v+1] & 1 \le s < NSeg_{FFS} - 1; z_{fs}(v) = -\delta \\ W_{II1} \cdot PD[c, NSeg - 1, v] + \\ W_{II2} \cdot PD[c, NSeg - 1, v+1] & s = NSeg_{FFS} - 1 \end{cases}$$

where $$n = int\left(\frac{s}{2}\right), A = int\left(\frac{s-1}{2}\right),$$

$W_{II1}$ and $W_{II2}$ are interpolation weights, and even(s)=1 when s even; 0 when s odd. The weights $W_{II1}$ and $W_{II2}$ are chosen such that $W_{II1}+W_{II2}=1$; usually we use $W_{II1}=0.5$ and $W_{II2}=0.5$, however other choices of weights are also possible. Note that, for a given value of v, and a given value of s not equal to 0 or $NSeg_{FFS}-1$, either the second line or the third line of Equation 8 is used, depending on the value of $z_{fs}(v)$ for the given view v.

Also, in equation (8) the parameters c, s, v stand for channel, segment, and view coordinates, respectively. In a typical CT system, the detector has in the order of 1000 channels (detectors per detector row), 64 segments (detector rows), and it collects in the order of 1000 views (projections) per revolution.

The two views are interpolated according to equation (8) and the interpolated view is obtained. The data processing and reconstruction processes carried out in unit 12 are performed using the interpolated views. Note that after the interpolation, the effective focal spot position ($zfs_{II}$) and source-object distance (determined by $R_{EB\_II}$) used in reconstruction are the nominal values.

Figure 4:
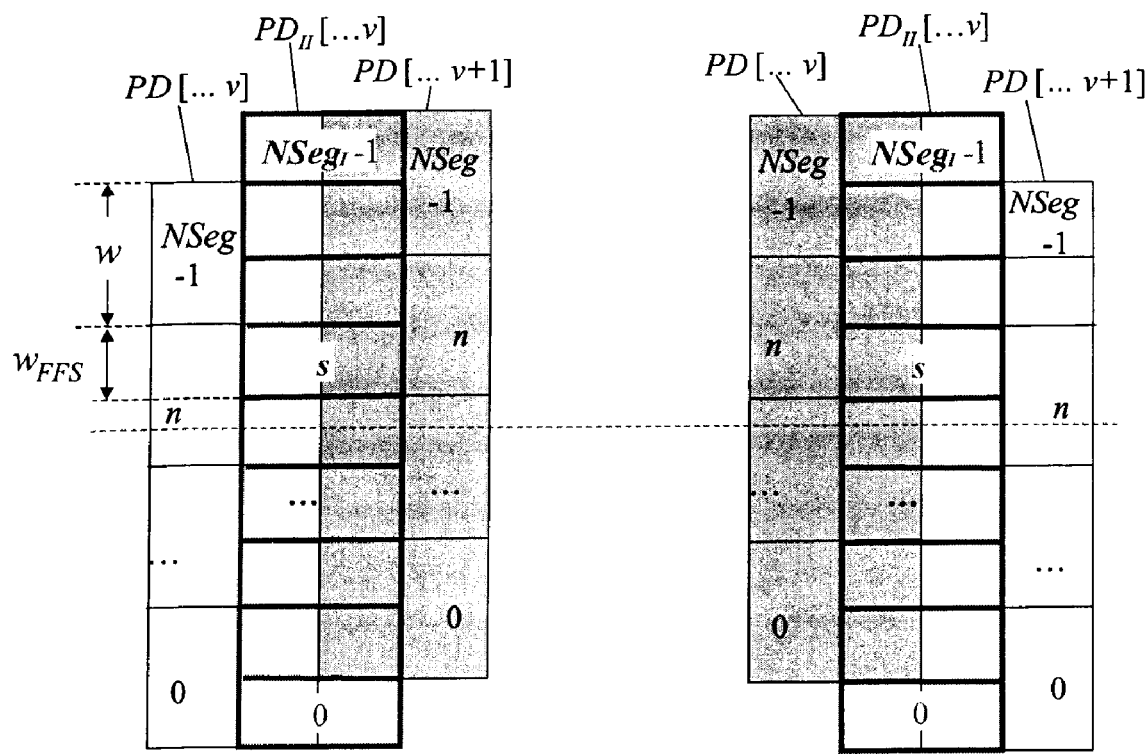
FIG. 4 is a diagram illustrating possible axial spatial orientations for adjacent views with resulting interpolated views.

The interpolation function depends on the axial orientation of views v and v+1. Two possible orientations exist, depending on the position of the flying focal spot for the two views. These are shown in FIG. 4. It is noted that FIG. 4 shows one column of channels for clarity while the interpolation is performed equally over all channels. Since the effective focal spot position alternates between +δ to −δ from one consecutive view to another, the orientations also alternate from one view to another.

Note that after the interpolation, the effective focal spot position ($zfs_H$) and source-object distance (determined by $R_{EB\_H}$) used in reconstruction are the nominal values. The first embodiment incorporates interpolation interlacing with dual flying focal spot position x-ray tube with focal positions in the z (axial, segment) direction. X-ray tubes with four focal spots, in both the axial and transaxial (channel) direction, also exist. Alternate embodiments include interlacing in the transaxial channel direction, as well as in interlacing in both the axial and transaxial direction.

The first embodiment is preferably implemented with a Feldkamp-type filtered backprojection reconstruction algorithm. Alternate embodiments can be incorporated with any arbitrary reconstruction algorithms for data obtained with flying focal spot x-ray tubes. These include other filtered backprojection algorithms, exact methods (such as described by Katsevitch and others), and statistical reconstruction algorithms.

The first embodiment is implemented with a third-generation, cone-beam type geometry. Alternate embodiments can be incorporated with any arbitrary geometry for data obtained with flying focal spot x-ray tubes, including parallel-beam or first, second, of fourth generation geometries.

Figure 1:
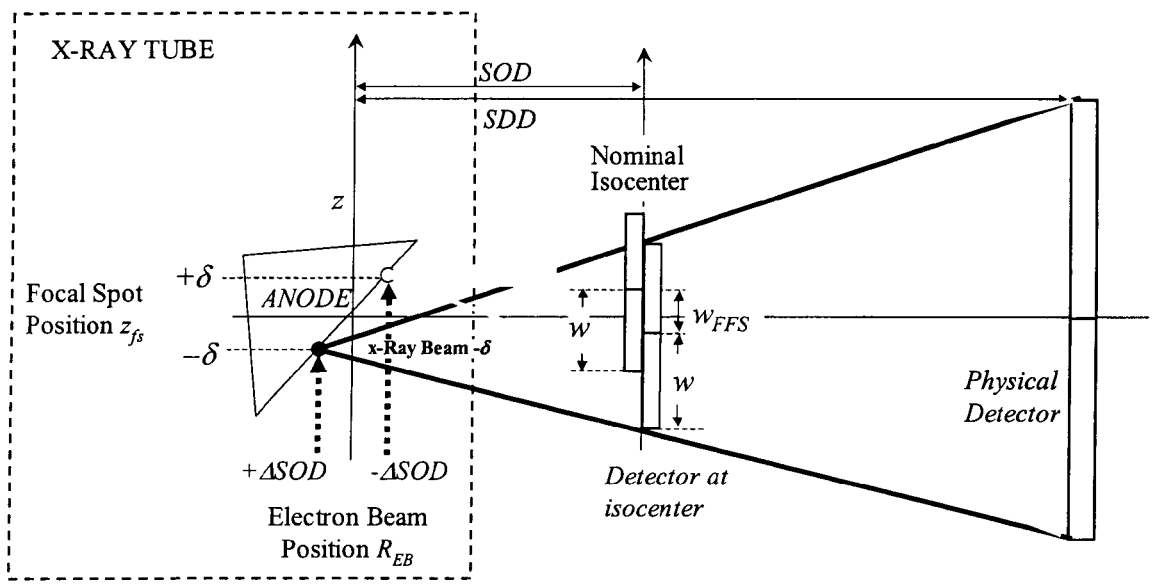
FIG. 1 is a diagram illustrating flying focal spot geometry.

The first embodiment is implemented with a flying focal spot x-ray tube anode oriented as shown in FIG. 1, where a positive focal spot position δ is associated with a negative ΔSOD. An alternate embodiment includes an x-ray tube with an anode upside down from FIG. 1; where a positive focal spot position δ is associated with a positive ΔSOD.

Two further alternate modifications are possible. First, the invention is implemented as part of backprojection and, second, as a separate process prior to backprojection. In both cases interlacing is performed on post-logged convolved data. Other modification of the first embodiment includes incorporation into different parts of the processing chain, such as before convolution.

The first embodiment is quick and simple, works in the native x-ray system geometry, does not require rebinning or resampling of data, and does not require doubling the number of views to obtain the same signal-to-noise ratio.

Figure 5:
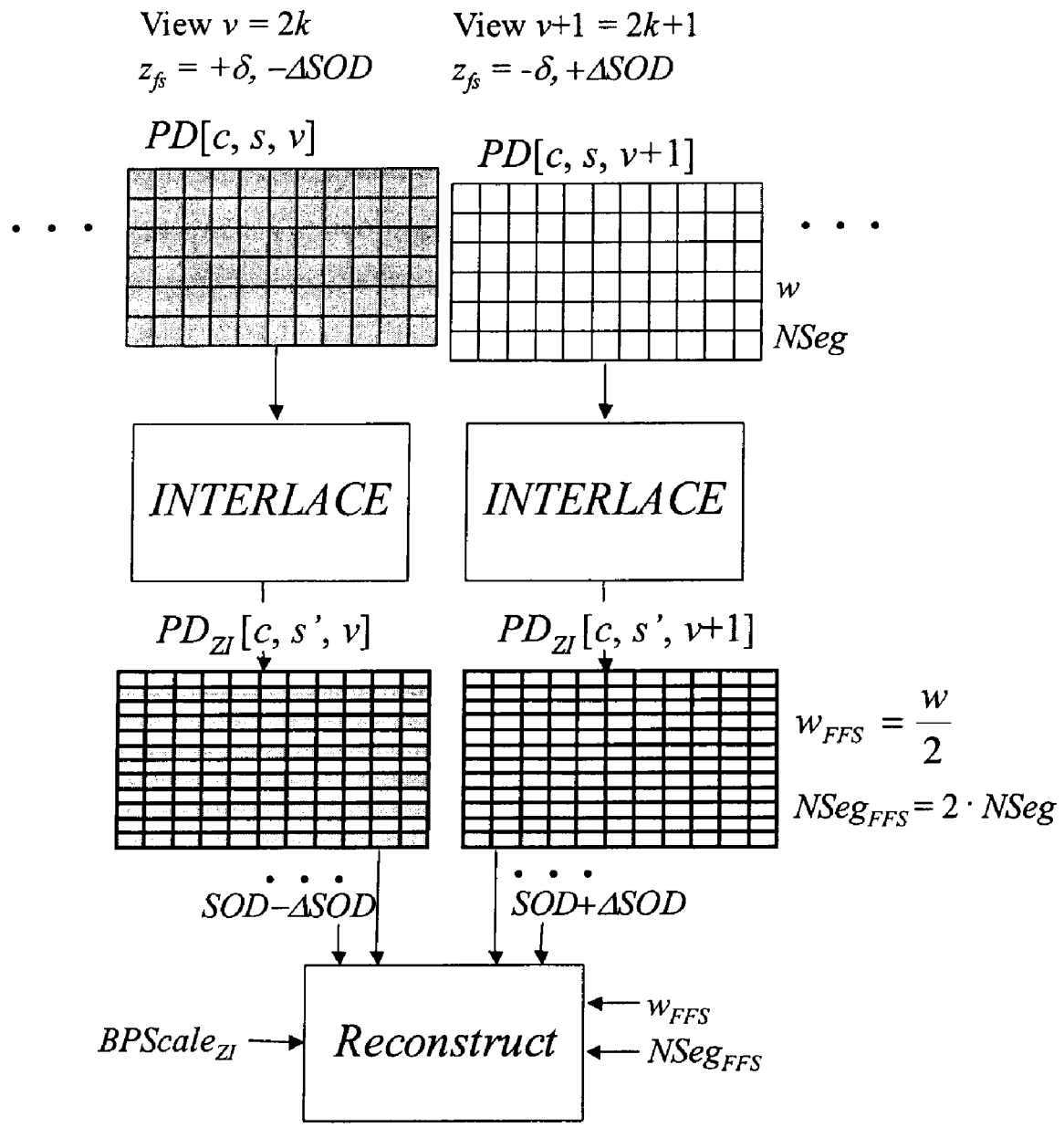
FIG. 5 is a diagram of interlacing processing according to a second embodiment of the invention.

A second embodiment is illustrated in FIG. 5. The embodiment uses a zero-interlacing technique. PD[ ] is post-logged, convolved projection data, and the number of segments in the projection data is doubled from NSeg to $NSeg_{FFS}$, along with halving the segment width from w to $w_{FFS}$ by the process of interlacing. This invention consists of the interlacing process, described in two forms: zero-interlacing and weighted zero-interlacing (though zero interlacing is really weighted zero-interlacing with zero weight). Once interlaced, each view is reconstructed with $w_{FFS}$, $NSEG_{FFS}$, SOD±ΔSOD, and $BPScale_{ZI}$ as the reconstruction parameters, where $BPScale_{ZI}$ is a backprojection scaling factor compensating for the interlaced values.

Figure 6:
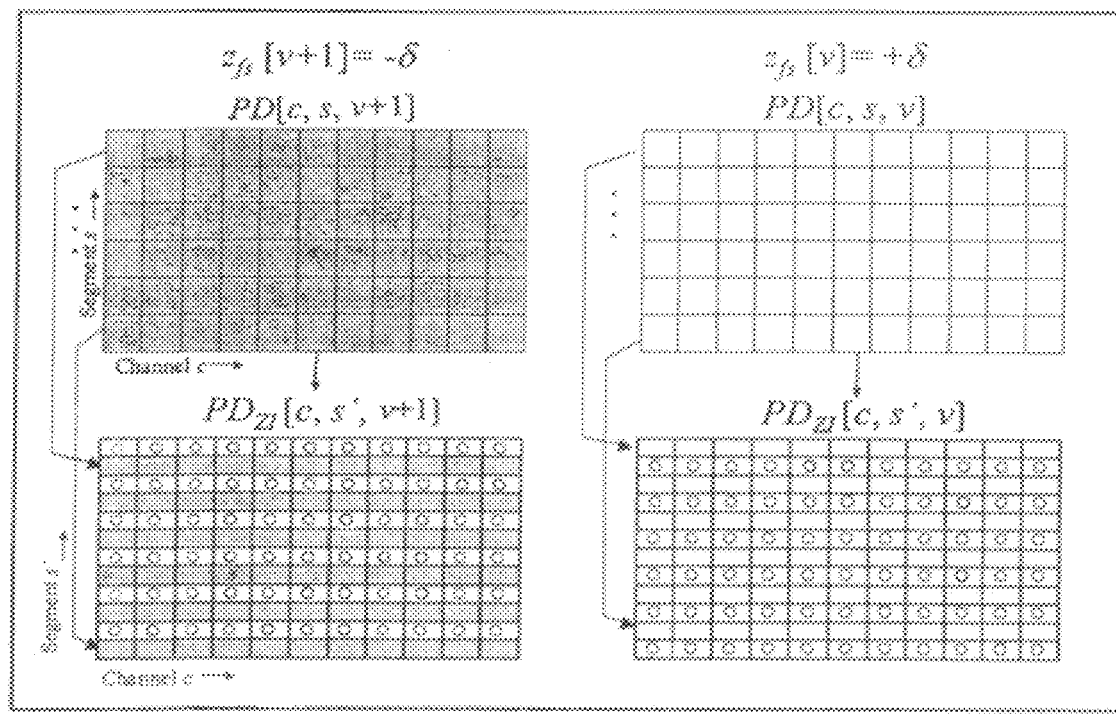
FIG. 6 is a diagram illustrating zero interlacing of projection data.

The details of zero-interlacing of adjacent views are shown in FIG. 6. The interlaced zero rows are a function of the focal spot position $z_{fs}$ as given in equation (9):

$$PD_{ZI}[c, s', v] = \begin{cases} 0, & z_{fs}[v] = +\delta, \ s' = 2s \\ PD[c, s, v], & z_{fs}[v] = +\delta, \ s' = 2s+1 \\ PD[c, s, v], & z_{fs}[v] = -\delta, \ s' = 2s \\ 0 & z_{fs}[v] = -\delta, \ s' = 2s+1 \end{cases} \quad (9)$$

The zero-interlaced projection data is then backprojected with either SOD+ΔSOD or SOD−ΔSOD, depending on focal spot position. In this case we use $BPScale_{ZI}$=2 BPScale, where BPScale is provided by the system (unit 12) and depends on many parameters, such as tube voltage, convolution kernel, etc.

Figure 7:
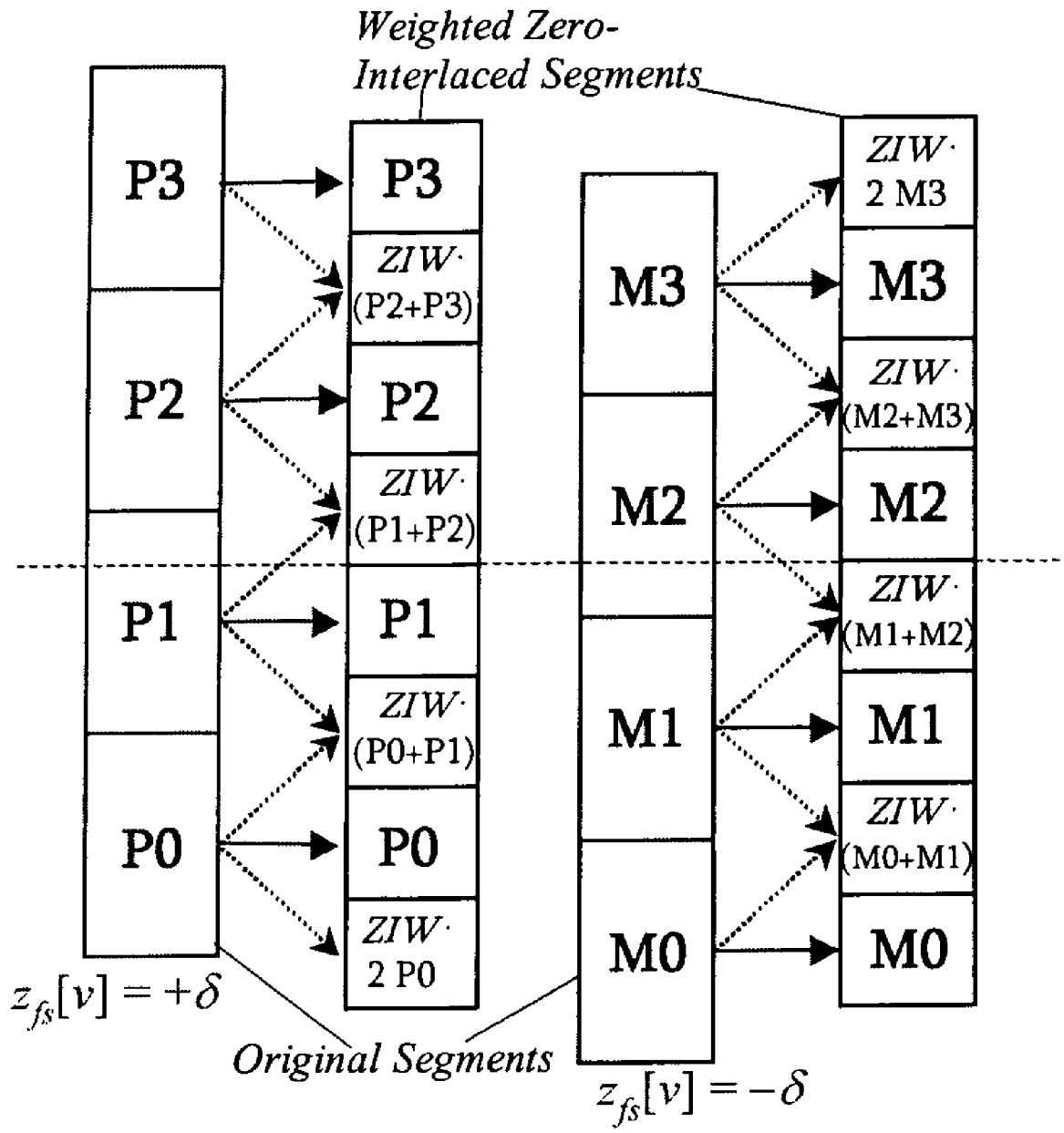
FIG. 7 is a diagram illustrating weighted zero-interlacing upsampling.

The weighted zero interlacing upsampling is shown in FIG. 7 and is performed according to equation (10):

$$PD_{ZIw}[c, s', v] = \begin{cases} W_{ZI} \cdot (PD[c, s, v] + PD[c, s+1, v]), & z_{fs}[v] = +\delta, \ s' = 2s \\ PD[c, s, v], & z_{fs}[v] = +\delta, \ s' = 2s+1 \\ PD[c, s, v], & z_{fs}[v] = -\delta, \ s' = 2s \\ W_{ZI} \cdot (PD[c, s, v] + PD[c, s+1, v]), & z_{fs}[v] = -\delta, \ s' = 2s+1 \end{cases} \quad (10)$$

FIG. 7 shows the case of NSeg upsampled from four to eight, with "P" representing segments acquired at $z_{fs}$=+δ and "M" segments at $z_{fs}$=−δ. Solid lines represent interpolation with weight 1, dashed lines represent interpolation with weight $W_{ZI}$.

$W_{ZI}$ can be varied from 0.0 to 0.5 to control the trade-off between resolution and windmill artifact reduction. Choosing $W_{ZI}$=0.0 (zero interlacing) obtains the best achievable resolution; however, due to sub-optimal sampling pattern the aliasing artifact may increase and windmill artifact reduction is not very strong. Increasing $W_{ZI}$ leads to a better windmill artifact reduction, but decrease in resolution (but resolution stays improved compared to the case without flying focal spot). With $W_{ZI}$=0.5 the sampling pattern becomes optimal for a given acquisition geometry, and the strongest reduction of the windmill artifact is achieved. Therefore, $W_{ZI}$ can be optimized for the best compromise between windmill artifact reduction and axial resolution improvement.

The backprojection scaling coefficient is also a function of $W_{ZI}$:

$$BPScale_{ZIw} = \frac{BPScale}{0.5 + W_{ZI}}$$

The second embodiment incorporates zero or weighted zero interlacing with a dual flying focal spot position x-ray tube with focal positions in the z (axial, segment) direction. X-ray tubes with four focal spots, in both the axial and transaxial (channel) direction, also exist. Modifications of the second embodiments include interlacing in the transaxial channel direction, as well as in interlacing in both the axial and transaxial direction.

The second embodiment is preferably implemented with a Feldkamp-type filtered backprojection reconstruction algorithm. Any arbitrary reconstruction algorithms for data obtained with flying focal spot x-ray tubes may also be used. These include other filtered backprojection algorithms, exact methods (such as described by Katsevitch and others), and statistical reconstruction algorithms.

The second embodiment is implemented with a third-generation, cone-beam type geometry. Any arbitrary geometry for data obtained with flying focal spot x-ray tubes, including parallel-beam or first, second, of fourth generation geometries may also be used with the second embodiment.

The current embodiment is implemented with a flying focal spot x-ray tube anode oriented as shown in FIG. 1, where a positive focal spot position δ is associated with a negative ΔSOD. An alternate embodiment includes an x-ray tube with an anode upside down from FIG. 1; where a positive focal spot position δ is associated with a positive ΔSOD.

Two modifications of the algorithm are possible: (1) implemented as part of backprojection and (2) a separate process prior to backprojection. In both cases interlacing is performed on post-logged convolved data. Other alternate embodiments include incorporation into different parts of the processing chain, such as before convolution, etc.

Numerous other modifications and variations of the present invention are possible in light of the above teachings.

It is therefore to be understood that within the scope of the appended claims, the invention may be practiced otherwise than as specifically described herein.

The invention claimed is:

1. A computed tomography apparatus, comprising:
a flying focal point x-ray source;
an x-ray detector disposed to receive x-rays from said x-ray source;
a unit to collect projection data generated by said detector; and
a processing unit configured to performing interpolation interlacing using said projection data and to reconstruct an image, wherein the processing unit is configured to perform interpolation to obtain interpolated projection data for a view in a manner dependent on a focal spot location of the view, so as to increase sampling in the axial direction without rebinning and resampling into a parallel geometry.

2. An apparatus as recited in claim 1, wherein said processing unit is configured to interpolate said projection data according to:

$$PD_{II}[c, s, v] = \begin{array}{ll} W_{II1} \cdot PD[c, 0, v] + & s = 0 \\ W_{II2} \cdot PD[c, 0, v+1] & \\ W_{II1} \cdot PD[c, A, v] + & 1 \leq s < NSeg_{FFS} - 1; \; z_{fs}(v) = +\delta \\ W_{II2} \cdot PD[c, n, v+1] & \\ W_{II1} \cdot PD[c, n, v] + & 1 \leq s < NSeg_{FFS} - 1; \; z_{fs}(v) = -\delta \\ W_{II2} \cdot PD[c, n, -even(s), v+1] & \\ W_{II1} \cdot PD[c, NSeg-1, v] + & s = NSeg_{FFS} - 1 \\ W_{II2} \cdot PD[c, NSeg-1, v+1] & \end{array}$$

where interpolated data $PD_{II}[c, s, v]$ is generated from projection data $PD[c, s, v]$ and $PD[c, s, v+1]$, c is channel, s is segment, v is view, $$n = int\left(\frac{s}{2}\right), A = int\left(\frac{s-1}{2}\right),$$

$W_{II1}$ and $W_{II2}$ are interpolation weights, NSeg and $NSeg_{FFS}$ are input and output number of segments, δ is an effect focal spot deviation, and even(s)=1 when s is even; and 0 when s is odd.

3. An apparatus as recited in claim 2, wherein said interpolation weights $W_{II1}$ and $W_{II2}$ are chosen such that $W_{II1} + W_{II2} = 1$.

4. An apparatus as recited in claim 2, wherein $W_{II1} = 0.5$ and $W_{II2} = 0.5$.

5. An apparatus as recited in claim 1, wherein said interpolation interlacing comprises zero interlacing upsampling and interpolates said projection data according to $$PD_{ZI}[c, s', v] = \begin{cases} 0, & z_{fs}[v] = +\delta, \; s' = 2s \\ PD[c, s, v], & z_{fs}[v] = +\delta, \; s' = 2s+1 \\ PD[c, s, v], & z_{fs}[v] = -\delta, \; s' = 2s \\ 0 & z_{fs}[v] = -\delta, \; s' = 2s+1 \end{cases}$$

where interpolated data $PD_{ZI}[c, s', v]$ is generated from projection data $PD[c, s, v]$, c is channel, s is segment, v is view, $z_{fs}$ is an effective focal spot position, and δ is an effective focal spot deviation.

6. An apparatus as recited in claim 1, wherein said interpolation interlacing comprises weighted zero interlacing upsampling and interpolates said projection data according to $$PD_{ZIw}[c, s', v] = \begin{cases} W_{ZI} \cdot (PD[c, s, v] + PD[c, s+1, v]), & z_{fs}[v] = +\delta, \; s' = 2s \\ PD[c, s, v], & z_{fs}[v] = +\delta, \; s' = 2s+1 \\ PD[c, s, v], & z_{fs}[v] = -\delta, \; s' = 2s \\ W_{ZI} \cdot (PD[c, s, v] + PD[c, s+1, v]), & z_{fs}[v] = -\delta, \; s' = 2s+1 \end{cases}$$

where interpolated data $PD_{ZIw}[c, s', v]$ is generated from projection data $PD[c, s, v]$, c is channel, s is segment, v is view, $z_{fs}$ is an effective focal spot position, and δ is an effective focal spot deviation and $W_{ZI}$ is a weight.

7. A computed tomography method, comprising:
exposing a subject to x-rays from a flying focal point x-ray source;
collecting projection data from said x-rays; and
performing interpolation interlacing using said projection data and to reconstruct an image, wherein the performing step includes performing interpolation to obtain interpolated projection data for a view in a manner dependent on a focal spot location of the view, so as to increase sampling in the axial direction without rebinning and resampling into a parallel geometry.

8. A method as recited in claim 7, comprising performing said interpolation interlacing according to:

$$PD_{II}[c, s, v] = \begin{array}{ll} W_{II1} \cdot PD[c, 0, v] + & s = 0 \\ W_{II2} \cdot PD[c, 0, v+1] & \\ W_{II1} \cdot PD[c, A, v] + & 1 \leq s < NSeg_{FFS} - 1; \; z_{fs}(v) = +\delta \\ W_{II2} \cdot PD[c, n, v+1] & \\ W_{II1} \cdot PD[c, n, v] + & 1 \leq s < NSeg_{FFS} - 1; \; z_{fs}(v) = -\delta \\ W_{II2} \cdot PD[c, n, -even(s), v+1] & \\ W_{II1} \cdot PD[c, NSeg-1, v] + & s = NSeg_{FFS} - 1 \\ W_{II2} \cdot PD[c, NSeg-1, v+1] & \end{array}$$

where interpolated data $PD_{II}[c, s, v]$ is generated from projection data $PD[c, s, v]$ and $PD[c, s, v+1]$, c is channel, s is segment, v is view $$n = int\left(\frac{s}{2}\right), A = int\left(\frac{s-1}{2}\right),$$

$W_{II1}$ and $W_{II2}$ are interpolation weights, NSeg and $NSeg_{FFS}$ are input and output number of segments, δ is an effect focal spot deviation, and even(s)=1 when s is even; and 0 when s is odd.

9. A method as recited in claim 8, comprising selecting said interpolation weights $W_{II1}$ and $W_{II2}$ such that $W_{II1} + W_{II2} = 1$.

10. A method as recited in claim 8, comprising selecting $W_{II1} = 0.5$ and $W_{II2} = 0.5$.

11. A method as recited in claim 7, wherein performing said interpolation interlacing comprises performing zero interlacing upsampling according to:

$$PD_{ZI}[c, s', v] = \begin{cases} 0, & z_{fs}[v] = +\delta, \ s' = 2s \\ PD[c, s, v], & z_{fs}[v] = +\delta, \ s' = 2s+1 \\ PD[c, s, v], & z_{fs}[v] = -\delta, \ s' = 2s \\ 0 & z_{fs}[v] = -\delta, \ s' = 2s+1 \end{cases}$$

where interpolated data $PD_{ZI}$ [c, s', v] is generated from projection data PD [c, s, v], c is channel, s is segment, v is view, $z_{fs}$ is an effective focal spot position, and $\delta$ is an effective focal spot deviation.

12. A method as recited in claim 7, wherein performing said interpolation interlacing comprises performing weighted zero interlacing upsampling according to:

$PD_{ZIw}[c, s', v] =$ $$\begin{cases} W_{ZI} \cdot (PD[c, s, v] + PD[c, s+1, v]), & z_{fs}[v] = +\delta, \ s' = 2s \\ PD[c, s, v], & z_{fs}[v] = +\delta, \ s' = 2s+1 \\ PD[c, s, v], & z_{fs}[v] = -\delta, \ s' = 2s \\ W_{ZI} \cdot (PD[c, s, v] + PD[c, s+1, v]), & z_{fs}[v] = -\delta, \ s' = 2s+1 \end{cases}$$

where interpolated data $PD_{ZIw}$ [c, s', v] is generated from projection data PD [c, s, v], c is channel, s is segment, v is view, $z_{fs}$ is an effective focal spot position, and $\delta$ is an effective focal spot deviation and $W_{ZI}$ is a weight.

13. A non-transitory computer-readable medium storing instructions that, when executed by a computer, cause the computer to perform a method comprising:
collecting projection data associated with x-rays from a flying focal point x-ray source exposing a subject; and
performing interpolation interlacing using said projection data and to reconstruct an image, wherein the performing step includes performing interpolation to obtain interpolated projection data for a view in a manner dependent on a focal spot location of the view, so as to increase sampling in the axial direction without rebinning and resampling into a parallel geometry.

14. A medium as recited in claim 13, wherein said method comprises performing said interpolation interlacing according to:

$PD_{II}[c, s, v] =$ $$\begin{cases} W_{II1} \cdot PD[c, 0, v] + & s = 0 \\ W_{II2} \cdot PD[c, 0, v+1] & \\ W_{II1} \cdot PD[c, A, v] + & 1 \leq s < NSeg_{FFS} - 1; \ z_{fs}(v) = +\delta \\ W_{II2} \cdot PD[c, n, v+1] & \\ W_{II1} \cdot PD[c, n, v] + & 1 \leq s < NSeg_{FFS} - 1; \ z_{fs}(v) = -\delta \\ W_{II2} \cdot PD[c, n, -even(s), v+1] & \\ W_{II1} \cdot PD[c, NSeg - 1, v] + & s = NSeg_{FFS} - 1 \\ W_{II2} \cdot PD[c, NSeg - 1, v+1] & \end{cases}$$

where interpolated data $PD_{II}$ [c, s, v] is generated from projection data PD [c, s, v] and PD [c, s, v+1], c is channel, s is segment, v is view, $$n = int\left(\frac{s}{2}\right), \ A = int\left(\frac{s-1}{2}\right),$$

$W_{II1}$ and $W_{II2}$ are interpolation weights, NSeg and $NSeg_{FFS}$ are input and output number of segments, $\delta$ is an effect focal spot deviation, and even(s)=1 when s is even, and 0 when s is odd.

15. A medium as recited in claim 14, wherein said method comprises selecting said interpolation weights $W_{II1}$ and $W_{II2}$ such that $W_{II1} + W_{II2} = 1$.

16. A medium as recited in claim 14, comprising selecting $W_{II1} = 0.5$ and $W_{II2} = 0.5$.

17. A medium as recited in claim 13, wherein said method comprises performing said interpolation interlacing comprises performing zero interlacing upsampling according to:

$$PD_{ZI}[c, s', v] = \begin{cases} 0, & z_{fs}[v] = +\delta, \ s' = 2s \\ PD[c, s, v], & z_{fs}[v] = +\delta, \ s' = 2s+1 \\ PD[c, s, v], & z_{fs}[v] = -\delta, \ s' = 2s \\ 0 & z_{fs}[v] = -\delta, \ s' = 2s+1 \end{cases}$$

where interpolated data $PD_{ZI}$ [c, s', v] is generated from projection data PD [c, s, v], c is channel, s is segment, v is view, $z_{fs}$ is an effective focal spot position, and $\delta$ is an effective focal spot deviation.

18. A medium as recited in claim 13, wherein performing said interpolation interlacing comprises performing weighted zero interlacing upsampling according to:

$PD_{ZIw}[c, s', v] =$ $$\begin{cases} W_{ZI} \cdot (PD[c, s, v] + PD[c, s+1, v]), & z_{fs}[v] = +\delta, \ s' = 2s \\ PD[c, s, v], & z_{fs}[v] = +\delta, \ s' = 2s+1 \\ PD[c, s, v], & z_{fs}[v] = -\delta, \ s' = 2s \\ W_{ZI} \cdot (PD[c, s, v] + PD[c, s+1, v]), & z_{fs}[v] = -\delta, \ s' = 2s+1 \end{cases}$$

where interpolated data $PD_{ZIw}$ [c, s', v] is generated from projection data PD [c, s, v], c is channel, s is segment, v is view, $z_{fs}$ is an effective focal spot position, and $\delta$ is an effective focal spot deviation and $W_{ZI}$ is a weight.

* * * * *